United States Patent [19]

Cesa

[11] Patent Number: 5,103,055
[45] Date of Patent: Apr. 7, 1992

[54] WATER-PROMOTED SYNTHESIS OF AMIDES FROM NITRILES AND ALCOHOLS

[75] Inventor: Mark C. Cesa, Cuyahoga, Ohio

[73] Assignee: The Standard Oil Company, Cleveland, Ohio

[21] Appl. No.: 521,615

[22] Filed: May 10, 1990

[51] Int. Cl.⁵ .......................................... C07C 231/06
[52] U.S. Cl. ................................... 564/130; 564/124; 564/182; 564/204; 564/215; 554/69
[58] Field of Search ............... 564/123, 124, 130, 131, 564/152, 153, 155, 156, 158–161, 167, 168, 170–172, 174, 176, 177, 179–192, 201–204, 207, 208, 215, 217–219, 221–224; 558/384, 388, 392–395, 401–404, 411, 415, 426–435, 445; 260/404

[56] References Cited

U.S. PATENT DOCUMENTS

| | | | |
|---|---|---|---|
| 2,320,089 | 1/1940 | Lichty | 564/131 |
| 2,719,176 | 9/1955 | Coover, Jr. et al. | 564/130 |
| 3,751,465 | 8/1973 | Takahashi et al. | 564/130 |
| 3,948,989 | 4/1976 | Drake | 564/130 |

FOREIGN PATENT DOCUMENTS

| | | | |
|---|---|---|---|
| 45-35525 | 11/1970 | Japan | 564/130 |
| 47-08050 | 3/1972 | Japan | 564/130 |
| 48-03813 | 2/1973 | Japan | 564/130 |
| 62-201853 | 9/1987 | Japan | 564/130 |

*Primary Examiner*—Glennon H. Hollrah
*Assistant Examiner*—Scott C. Rand
*Attorney, Agent, or Firm*—C. S. Lynch; M. F. Esposito; L. W. Evans

[57] ABSTRACT

Disclosed is a method which comprises the reaction in a reaction zone of a nitrile, RCN, with a hydroxyl compound, R'OH, in the presence of water introduced into the reaction zone in the amount of more than 0.15 mole and up to 10 moles, per mole of RCN introduced to the reaction zone, thereby producing a reaction mixture containing at least one amide selected from R—CONHR' and R—CON(R')$_2$, wherein each of R and R' contains no acetylenic unsaturation and 1 to 30 carbon atoms, each of R and R' is independently selected from a hydrocarbyl group and a hydrocarbyl group that is substituted with a group selected from cyano, carbamoyl, hydrocarbylcarbamoyl, dihydrocarbylcarbamoyl, and hydroxyl, and said reaction is effected in the presence of said water (1) without any catalyst for said reaction being introduced into said reaction zone or (2) with a catalyst being introduced into said reaction zone selected from elements of Groups 6, 8, 9, 10, 11 and 12, the elements Zr, V, Mn, Si, Al, Sn, Pb, Sb, and Bi; oxides, peroxides, sulfides, oxyhalogen compounds, hydroxides, and salts of inorganic acids of any one of the foregoing elements; and mixtures of any of the foregoing.

14 Claims, No Drawings

WATER-PROMOTED SYNTHESIS OF AMIDES FROM NITRILES AND ALCOHOLS

This invention relates to the synthesis of N-substituted amides by condensation of nitriles with certain organic hydroxyl compounds promoted by water.

The important industrial solvent, N,N-dimethylacetamide, is currently prepared industrially from acetic acid and dimethylamine. It is a superior organic solvent, with high boiling range and good thermal stability relative to other amides such as dimethylformamide. The current DMAC synthesis suffers from relatively high raw material costs. As a result, DMAC has a high price (about $1.00 per pound). This high price precludes use of DMAC in many applications where relatively inferior but lower priced solvents are used.

The process of the present invention has the potential to lower N-substituted amides production costs substantially because of the much lower prices of the starting materials compared with the price of the raw materials of the current synthetic method, thus offering the potential for growth of DMAC demand into applications where its superior properties would be an advantage.

It is an object of the present invention to improve the process of making N-substituted amides.

It is a further object of the invention to lower the cost of making N-substituted amides by condensing nitriles with alcohols in the presence of water as a promoter.

Other objects, as well as aspects and advantages, of the invention will become apparent from a study of the specification, including the specific examples and the claims.

The foregoing and other objects are realized by the present invention according to which there is provided a method which comprises the reaction in a reaction zone of a nitrile, RCN, with a hydroxyl compound, R'OH, in the presence of water introduced into the reaction zone in the amount of more than 0.15 mole (usually at least 0.17 mole) and up to 10 moles, per mole of RCN introduced to the reaction zone, thereby producing a reaction mixture containing at least one amide selected from R—CONHR' and R—CON(R')$_2$, wherein each of R and R' contains no acetylenic unsaturation and 1 to 30 (usually 1 to 12) carbon atoms, each of R and R' is independently selected from a hydrocarbyl group and a hydrocarbyl group that is substituted with a group selected from cyano, carbamoyl, hydrocarbylcarbamoyl, dihydrocarbylcarbamoyl, and hydroxyl, and said reaction is effected in the presence of said water (1) without any catalyst for said reaction being introduced into said reaction zone or (2) with a catalyst being introduced into said reaction zone selected from elements of Groups 6, 8, 9, 10, 11 and 12, the elements Zr, V, Mn, Si, Al, Sn, Pb, Sb, and Bi; oxides, peroxides, sulfides, oxyhalogen compounds, hydroxides, and salts of inorganic acids of any one of the foregoing elements; and mixtures of any of the foregoing.

In U.S. Pat. No. 2,601,387 a large amount of water to dilute the sulfuric acid catalyst is disclosed in the reaction of a tertiary alcohol and a nitrile such as acetonitrile to make an N-tert-alkyl amide. Dilution of the acid with water does not promote the reaction since an increased temperature is necessary.

In the process of the present invention a number of side reactions occur, producing numerous by-products in addition to the N-substituted amides R—CONHR' and R—CON(R')$_2$. Typically, such by-products include mono-, di- and trimethyl amines, methyl acetate, water, acetic acid, and acetamide, where the charge reactants are acetonitrile and methanol, for instance.

In one aspect of practising the invention we contemplate removal from the reaction zone effluent the R—CON(R')$_2$ product and any water not needed; the rest of the effluent is combined with fresh RCN, R'OH and the desired amount of water and further reacted, thus increasing the overall yield and selectivity to R—CON(R')$_2$ based on RCN charged.

In another aspect of the invention we contemplate charging to the reaction zone a crude cut from the effluent of an ammoxidation reaction for making acrylonitrile, for instance, from propylene or from propane. Thus, a partially purified acetonitrile cut separated from the ammoxidation reactor effluent can be all or part of the acrylonitrile charge to the reaction zone of this invention. This cut is mainly acetonitrile and water, but also contains small amounts of other components such as acrylonitrile, methacrylonitrile, propionitrile, pyridine, methyl-substituted pyridine(s), oxazole, pyrazine, benzonitrile, cyanopyridine, cyano-furans and aniline.

The condensation of nitriles with alcohols to form N-substituted amides is known as the Ritter reaction. Typical Ritter reaction catalysts are mineral acids, such as H$_2$SO$_4$ or H$_3$PO$_4$. The Ritter reaction is usually thought of as a reaction between a nitrile and a secondary or tertiary alcohol, which can readily form a carbonium ion in the presence of mineral acid. The carbonium ion then reacts with the nitrile in the key step in amide formation.

Formation of amides from nitriles and primary alcohols, e.g. methanol, requires more severe conditions. A series of patents to Asahi (U.S. Pat. No. 3,751,465; JP 73 03,813; GB 1,229,618, Chemical Abstracts 74, 124883n and 76, 139955c) describe the use of catalysts such as transition metal salts for synthesis of DMAC from acetonitrile and methanol at high temperatures (up to 400° C. or higher) in stirred autoclaves.

In an article by Y. Fukuoka and N. Kominami in "Chemtech," November 1972, pp. 670–674 it is disclosed that added water increased the yield of N,N-dialkylformamide and of N-methylformamide in the reaction of HCN with methanol when using certain catalysts such as TiCl$_4$ and Ti(OH)$_4$. In Japanese Patent Publication 48-3813, published Feb. 2, 1973, by the same Fukuoka, and others, relating to the reaction of alcohols with nitriles, R—CN, wherein R is an alkyl radical having 1–6 C atoms, it is stated specifically that water should be removed as it is formed, or periodically. This is a teaching away from the process of the present invention, which teaches promoting the reaction by adding water to the initial reaction mixture of such a nitrile with a hydroxyl-containing compound, R'OH, defined herein.

Indeed, in U.S. Pat. No. 3,751,465 to the same Fukuoka, and others, it is noted, in reference to the reaction of HCN with an alcohol to make a dialkyl formamide, that hydrogen cyanide is "utterly different in chemical behavior from the nitrile." See col. 1, first paragraph and col. 5, first paragraph. Moreover, in U.S. Pat. No. 3,882,175 issued May 6, 1975 (claiming 1970 priorities in Japan), having as inventors, K. Sasaki and the same Y. Fukuoka and N. Kominami who authored the 1972 "Chemtech" article referred to, supra, it is taught that the reaction of HCN with an alcohol to make an N,N- dialkylformamide, using as catalysts certain titanium compounds, is improved by the initial presence of added water. See claim 1 and column 2 of the specification. This patent also states in the last full paragraph of column 2:

> Such favorable effect due to the addition of water in the reaction system can be observed only in case where the alcohol is reacted with hydrocyanic acid, but are not observed in cases *where the alcohol is reacted with an alkyl nitrile*. Moreover, it should be noted that, in case the alcohol is reacted with an alkyl nitrile, the addition or presence of water has an *adverse effect* on the reaction and, as distinguished from the process of the present invention, the removal of water is required to obtain an increased yield of the desired product. (emphasis added.)

In contrast in the presently claimed process water is not removed during the reaction of the defined nitrile with the alcohol to make the claimed N-substituted amides. Moreover, as to the favorable effect of water in the HCN reaction claimed in this U.S. Pat. No. 3,882,175, it is noted in column 3, lines 30-33 that > "the favorable effect due to the addition of water and the specific temperatures in the present invention can be obtained only when a titanium compound is employed as a catalyst." (emphasis added.)

Thus the art taken as a whole teaches that the introduction of water in the reaction of alkyl nitriles with alcohols to produce N-substituted amides has no beneficial effect and in fact has an adverse effect on product yield, contrary to my invention.

This invention is based on the surprising discovery that addition of substantial amounts of water to nitrile/alcohol reaction mixtures, with as well as without byproduct recycle, and with as well as without catalyst, results in a very significant acceleration of the amide synthesis reaction rate and, even more surprisingly, improvement in N-substituted amide selectivity and yield based on RCN. The use of water has several important advantages. When used in the absence of catalyst, water avoids the problems with corrosion caused by mineral acids or organic acids as catalysts; water is also stable to reaction conditions, in contrast to many transition metal salt catalysts, which can decompose under amide synthesis reaction conditions. In the presence of catalyst, water enhances product selectivity or yield. These results are surprising, both because of the art teachings and also because of the expectation that water would act to remove amide products from reaction mixtures by hydrolysis. These results will be illustrated herein.

According to the present invention, the water-promoted synthesis of amides from nitriles and alcohols can be carried out in either the vapor phase or in the liquid phase, at atmospheric pressure or reduced or elevated pressure, in a batch mode, flow mode or continuous stirred reactor mode. If byproduct recycle is desired, the recycle process can be carried out continuously or in a batch mode. In an especially effective embodiment of the invention, applied to the synthesis of, for example, N,N-dimethylacetamide (DMAC) from acetonitrile and methanol, a continuous stirred reactor system can be used in which reaction byproducts and unreacted starting materials (recovered by distillation) are recycled to the reaction zone along with water and fresh starting materials, with flows balanced so that an essentially constant DMAC synthesis rate is established with essentially no net byproduct synthesis.

The presence of inert diluents for any of the starting materials is within the scope of the invention. For example, the use of nitrogen or other inert gas in the reaction zone is permitted, and is favored in high-temperature liquid phase conditions to minimize unwanted side reactions. Also, the use of inert solvents with the reactants such as, for example (but not restricted to), alkanes and aromatic hydrocarbons is within the scope of the invention.

The reactants can be employed from the beginning of the reaction in the full amounts required for the reaction, or the reactants can be introduced to the reaction zone successively or stepwise during the course of the reaction.

While the use of catalysts is not necessary for the water-promoted amide synthesis of this invention, it is found that water can improve N-substituted amide yield or selectivity in reactions catalyzed with the noted catalysts. The "Groups" in the claims refer to the Periodic Table of the Elements that numbers the groups from 1 to 18, appearing in *Chemical and Engineering News*, Feb. 4, 1985, p. 27. Such catalysts can be soluble in the reaction medium or insoluble, and may be used in liquid phase and vapor phase operation. The listed catalysts can also be supported on organic polymers or inorganic oxide supports if desired.

The process of this invention can be carried out at from 20° to 600° C. Optimum temperatures depend on the particular reactants and other parameters easily determined by routine test. For instance, primary alcohols usually require higher temperatures than secondary and tertiary alcohols.

Pressures can range from 0.1 to 200 atmospheres or more. In liquid phase runs carried out in pressure vessels with low-boiling reactants, high reaction temperatures required for sufficient reaction rates result in pressures well above 1 atmosphere, as in the case of the specific examples herein.

The alcohol/nitrile mole ratio can range from 0.1 to 20, but usual ratios range from 1.0 to 10. Lower amounts of alcohol relative to nitrile result in promotion of formation of N-monosubstituted amide, and higher amounts sometimes can alcoholyze amide products, lowering yield of desired product. It should be noted that formation of appreciable amounts of N-monosubstituted amide is not necessarily a disadvantage. First, if this is desired as a product, or in the second instance if a recycle process be used. In the latter event the N-substituted amide is a very efficacious feed to the reaction zone, where it helps maintain the equilibrium between this by-product and all other reaction products.

The amide products of this invention have a variety of uses. For example, N,N-dimethylacetamide (DMAC) is an important industrial solvent used in acrylic fiber spinning and in pharmaceutical synthesis. Other amides are useful monomers, reaction solvents, and synthetic intermediates.

The process of the present invention does not involve the intentional addition of ammonia or molecular oxygen into the reaction zone, because of loss of products by oxidation.

The following examples of the invention are exemplary and should not be taken as in any way limiting.

EXAMPLE 1

A mixture of acetonitrile (32.85 g, 0.8002 mol), methanol (33.31 g, 1.0396 mol), and water (14.41 g, 0.7999 mol) was placed in a stainless steel autoclave of 300 mL internal volume. The reactor was sealed, and the reaction mixture was purged with nitrogen through a dip tube for 30 minutes. The reactor was then heated to 350° C., and the reaction mixture was stirred vigorously for 2.5 hours. The temperature of the reaction mixture reached 359° C. during this time. The reactor was then cooled, and the reaction mixture was analyzed by gas chromatography. Conversion of methanol was 89.5% and conversion of acetonitrile was 94.2%. Product yields (based on acetonitrile) were as follows: methylamine 0.4%, dimethylamine 10.5%, methyl acetate 0.5%, N,N-dimethylacetamide (DMAC) 21.7%, acetic acid 13.9%, N-methylacetamide 40.3%, and acetamide 17.6%.

COMPARATIVE EXAMPLE A

A mixture of acetonitrile (42.15 g, 1.027 mol) and methanol (42.77 g, 1.335 mol) was placed in a stainless steel autoclave of 300 mL internal volume. The reactor was sealed, and the reaction mixture was purged with nitrogen through a dip tube for 30 minutes. The reactor was then heated to 360° C., and the reaction mixture was stirred vigorously for 1.0 hour. The temperature of the reaction mixture reached 360° C. during this time. The reactor was then cooled, and the reaction mixture was analyzed by gas chromatography. Conversion of methanol was 18.2% and conversion of acetonitrile was 14.6%. Product yields (based on acetonitrile) were as follows: methylamine 0.4%, dimethylamine 0, methyl acetate 3.0%, N,N-dimethylacetamide (DMAC) 0.04%, acetic acid 0.1%, N-methylacetamide 0.3%, and acetamide 1.8%.

COMPARATIVE EXAMPLE B

A mixture of acetonitrile (31.57 g, 7690 mol) and methanol (32.04 g, 0.9999 mol) was placed in a stainless steel autoclave of 300 mL internal volume. The reactor was sealed, and the reaction mixture was purged with nitrogen through a dip tube for 30 minutes. The reactor was then heated to 350° C., and the reaction mixture was stirred vigorously for 4 hours. The temperature of the reaction mixture reached 353° C. during this time. The reactor was then cooled, and the reaction mixture was analyzed by gas chromatography. Conversion of methanol was 37.8% and conversion of acetonitrile was 20.4%. Product yields (based on acetonitrile) were as follows: methylamine 2.6%, dimethylamine 5.6%, methyl acetate 12.2%, N,N-dimethylacetamide (DMAC) 0.5%, acetic acid 0.3%, N-methylacetamide 3.3%, and acetamide 4.1%.

EXAMPLE 2

To simulate recycle conditions, a mixture of acetonitrile (12.13 g, 0.2955 mol), methanol (19.50 g, 0.6086 mol), water (10.51 g, 0.5834 mol), methylamine (0.68 g, 0.0219 mol), dimethylamine (6.32 g, 0.1402 mol), methyl acetate (1.01 g, 0.0136 mol), acetic acid (3.51 g, 0.0584 mol), N-methylacetamide (25.90 g, 0.3543 mol), and acetamide (19.03 g, 0.3222 mol) was placed in a stainless steel autoclave of 300 mL internal volume. The reactor was sealed, and the reaction mixture was purged with nitrogen through a dip tube for 30 minutes. The reactor was then heated to 350° C., and the reaction mixture was stirred vigorously for 2 hours. The temperature of the reaction mixture reached 370° C. during this time. The reactor was then cooled, and the reaction mixture was analyzed by gas chromatography. Conversion of methanol was 89.6% and conversion of acetonitrile was 85.2%. N,N-dimethylacetamide yield (based on acetonitrile) was 77.6%.

COMPARATIVE EXAMPLE C

To simulate recycle conditions, a mixture of acetonitrile (12.12 g, 0.2952 mol), methanol (19.51 g, 0.6089 mol), methylamine (0.71 g, 0.0229 mol), dimethylamine (6.73 g, 0.1493 mol), methyl acetate (1.01 g, 0.0136 mol) acetic acid (3.58 g, 0.0596 mol), N-methylacetamide (25.92 g, 0.3546 mol), and acetamide (19.05 g, 0.3225 mol) was placed in a stainless steel autoclave of 300 mL internal volume. The reactor was sealed, and the reaction mixture was purged with nitrogen through a dip tube for 30 minutes. The reactor was then heated to 350° C., and the reaction mixture was stirred vigorously for 3 hours. The temperature of the reaction mixture reached 376° C. during this time. The reactor was then cooled, and the reaction mixture was analyzed by gas chromatography. Conversion of methanol was 71.3% and conversion of acetonitrile was 71.3%. N,N-dimethylacetamide yield (based on acetonitrile) was 85.1%.

EXAMPLE 3

A mixture of acetonitrile (41.7 g, 1.016 mol) and methanol (43.8 g, 1.366 mol) and $CoCl_2 \cdot 6H_2O$ (7.07 g, 29.7 mmol; 0.1782 mol water) was placed in a stainless steel autoclave of 300 mL internal volume. The reactor was sealed, and the reaction mixture was purged with nitrogen through a dip tube for 30 minutes. The reactor was then heated to 350° C., and the reaction mixture was stirred vigorously for 1 hour. The temperature of the reaction mixture reached 355° C. during this time. The reactor was then cooled, and the reaction mixture was analyzed by gas chromatography. Conversion of methanol was 90.1% and conversion of acetonitrile was 95.1%. Product yields (based on acetonitrile) were as follows: methylamine 0.1%, dimethylamine 5.9%, methyl acetate 0.7%, N,N-dimethylacetamide (DMAC) 22.8%, acetic acid 0.7%, N-methylacetamide 40.9%, and acetamide 13.0%. The product mixture was fractionally distilled to give 5.53 g of material boiling below 63° C. at atmospheric pressure and containing methylamine, dimethylamine, methyl acetate, and unreacted acetonitrile and methanol.

COMPARATIVE EXAMPLE D

A mixture of acetonitrile (41.06 g, 1.0002 mol) and methanol (41.67 g, 1.3005 mol) and anhydrous $CoCl_2$ (3.96 g, 0.0305 mol) was placed in a stainless steel autoclave of 300 mL internal volume. The reactor was sealed, and the reaction mixture was purged with nitrogen through a dip tube for 30 minutes. The reactor was then heated to 350° C., and the reaction mixture was stirred vigorously for 4 hours. The temperature of the reaction mixture reached 387° C. during this time. The reactor was then cooled, and the reaction mixture was analyzed by gas chromatography. Conversion of methanol was 99.5% and conversion of acetonitrile was 97.8%. Product yields (based on acetonitrile) were as follows: methylamine 2.3%, dimethylamine 10.2%, methyl acetate 0, N,N-dimethylacetamide (DMAC) 12.0%, acetic acid 5.4%, N-methylacetamide 48.6%, and acetamide 20.6%.

EXAMPLE 4

To simulate recycle conditions, a mixture of acetonitrile (11.94 g, 0.291 mol), methanol (19.04 g, 0.594 mol), $CoCl_2.6H_2O$ (6.99 g, 29.4 mmol, water content 176.4 mmol), 4.92 g of a mixture of methylamine, dimethylamine, methyl acetate, and unreacted acetonitrile and methanol (the distillate fraction from Example 3), acetic acid (2.64 g, 0.0440 mol), N-methylacetamide (37.11 g, 0.508 mol), and acetamide (11.34 g, 0.192 mol) was placed in a stainless steel autoclave of 300 mL internal volume. The reactor was sealed, and the reaction mixture was purged with nitrogen through a dip tube for 30 minutes. The reactor was then heated to 350° C., and the reaction mixture was stirred vigorously for 1 hour. The temperature of the reaction mixture reached 369° C. during this time. The reactor was then cooled, and the reaction mixture was analyzed by gas chromatography. Conversion of methanol was 81.6% and conversion of acetonitrile was 87.4%. N,N-dimethylacetamide yield (based on acetonitrile) was 58.6%.

COMPARATIVE EXAMPLE E

To simulate recycle conditions, a mixture of acetonitrile (12.13 g, 0.2955 mol), methanol (19.54 g, 0.6098 mol), anhydrous $CoCl_2$ (4.0 g, 0.0308 mol), methylamine (0.96 g, 0.0309 mol), dimethylamine (5.01 g, 0.111 mol), acetic acid (3.35 g, 0.0558 mol), N-methylacetamide (35.51 g, 0.4858 mol), and acetamide (12.11 g, 0.2050 mol) was placed in a stainless steel autoclave of 300 mL internal volume. The reactor was sealed, and the reaction mixture was purged with nitrogen through a dip tube for 30 minutes. The reactor was then heated to 350° C., and the reaction mixture was stirred vigorously for 2.75 hours. The temperature of the reaction mixture reached 394° C. during this time. The reactor was then cooled, and the reaction mixture was analyzed by gas chromatography. Conversion of methanol was 98.8% and conversion of acetonitrile was 72.9%. N,N-dimethylacetamide yield (based on acetonitrile) was 33.1%.

EXAMPLE 5

A mixture of acetonitrile (41.05 g, 0.9999 mol) and methanol (41.67 g, 1.3005 mol), mordenite (3.28 g), and water (18.04 g, 1.0014 mol) was placed in a stainless steel autoclave of 300 mL internal volume. The reactor was sealed, and the reaction mixture was purged with nitrogen through a dip tube for 30 minutes. The reactor was then heated, and the reaction mixture was stirred vigorously for 3 hours. The temperature of the reaction mixture reached 345° C. during this time. The reactor was then cooled, and the reaction mixture was analyzed by gas chromatography. Conversion of methanol was 92.4% and conversion of acetonitrile was 92.8%. Product yields (based on acetonitrile) were as follows: methylamine 0.5%, dimethylamine 7.9%, methyl acetate 0.5%, N,N-dimethylacetamide (DMAC) 19.1%, acetic acid 12.5%, N-methylacetamide 37.8%, and acetamide 11.4%.

EXAMPLE 6

A 46.13 g sample of crude acetonitrile of approximate composition 49.3 weight % acetonitrile, 42.3 weight % water, 0.3 weight % HCN, and the remainder acrylonitrile, propionitrile, methanol, oxazole, methacrylonitrile, pyridine, pyrazine, butenenitrile, and methylpyridines was combined with methanol (20.03 g, 0.6251 mol), and the mixture was placed in a stainless steel autoclave of 300 mL internal volume. The reactor was sealed, and the reaction mixture was purged with nitrogen through a dip tube for 30 minutes. The reactor was then heated to 350° C., and the reaction mixture was stirred vigorously for 2.5 hours. The temperature of the reaction mixture reached 354° C. during this time. The reactor was then cooled, and the reaction mixture was analyzed by gas chromatography. Conversion of methanol was 90.6% and conversion of acetonitrile was 92.0%. Product yields (based on acetonitrile) were as follows: methylamine 0.3%, dimethylamine 4.9%, methyl acetate 0.6%, N,N-dimethylacetamide (DMAC) 14.7%, acetic acid 23.3%, N-methylacetamide 40.3%, and acetamide 22.2%.

EXAMPLE 7

To simulate recycle conditions, a 15.42 g sample of crude acetonitrile of approximate composition 49.3 weight % acetonitrile, 42.3 weight % water, 0.3 weight % HCN, and the remainder acrylonitrile, propionitrile, methanol, oxazole, methacrylonitrile, pyridine, pyrazine, butenenitrile, and methylpyridines was combined with methanol (11.88 g, 0.3708 mol), methylamine (0.34 g, 0.0109 mol), dimethylamine (2.01 g, 0.0446 mol), methyl acetate (0.29 g, 0.0039 mol), acetic acid (3.94 g, 0.0656 mol), N-methylacetamide (16.47 g, 0.2253 mol), and acetamide (7.33 g, 0.1241 mol) was placed in a stainless steel autoclave of 300 mL internal volume. The reactor was sealed, and the reaction mixture was purged with nitrogen through a dip tube for 30 minutes. The reactor was then heated to 350° C., and the reaction mixture was stirred vigorously for 2 hours. The temperature of the reaction mixture reached 370° C. during this time. The reactor was then cooled, and the reaction mixture was analyzed by gas chromatography. Conversion of methanol was 91.3% and conversion of acetonitrile was 83.8%. N,N-dimethylacetamide yield (based on acetonitrile) was 67.9%.

In the following examples 8–11 the amount of water (as percent of acetonitrile charged) was about 33 percent, the reaction temperature was 380° C., and the reaction time was 4.5 hours, but the ratio of methanol to nitrile was varied.

EXAMPLE 8

A mixture of acetonitrile (34.89 g, 0.8499 mol), methanol (27.24 g, 0.850 mol), and water (4.59 g, 0.2548 mol) was placed in a stainless steel autoclave of 300 mL internal volume. The reactor was sealed, and the reaction mixture was purged with nitrogen through a dip tube for 30 minutes. The reactor was then heated to 350° C. and the reaction mixture was stirred vigorously for 4.5 hours. The temperature of the reaction mixture reached 383° C. during this time. The reactor was then cooled, and the reaction mixture was analyzed by gas chromatography. Conversion of methanol was 90.3% and conversion of acetonitrile was 78.3%. Product selectivities (based on acetonitrile) were as follows: methyl acetate 2.3%, N,N-dimethylacetamide (DMAC) 26.4%, acetic acid 12.5%, N-methylacetamide 28.4%, and acetamide 28.6%.

EXAMPLE 9

A mixture of acetonitrile (31.59 g, 0.7695 mol), methanol (32.05 g, 1.0002 mol), and water (4.62 g, 0.2565 mol) was placed in a stainless steel autoclave of 300 mL internal volume. The reactor was sealed, and the reaction mixture was purged with nitrogen through a dip tube for 30 minutes. The reactor was then heated to 350° C., and the reaction mixture was stirred vigorously for 4.5 hours. The temperature of the reaction mixture reached 385° C. during this time. The reactor was then cooled, and the reaction mixture was analyzed by gas chromatography. Conversion of methanol was 90.0% and conversion of acetonitrile was 86.2%. Product selectivities (based on acetonitrile) were as follows: methyl acetate 1.7%, N,N-dimethylacetamide (DMAC) 32.0%, acetic acid 16.0%, N-methylacetamide 28.2%, and acetamide 21.2%.

EXAMPLE 10

A mixture of acetonitrile (24.64 g, 0.6002 mol), methanol (38.46 g 1.2003 mol), and water (3.24 g, 0.1798 mol) was placed in a stainless steel autoclave of 300 mL internal volume. The reactor was sealed, and the reaction mixture was purged with nitrogen through a dip tube for 30 minutes. The reactor was the heated to 350° C., and the reaction mixture was stirred vigorously for 4.5 hours. The temperature of the reaction mixture reached 383° C. during this time. The reactor was then cooled, and the reaction mixture was analyzed by gas chromatography. Conversion of methanol was 89.9% and conversion of acetonitrile was 90.2%. Product selectivities (based on acetonitrile) were as follows: methyl acetate 4.0%, N,N-dimethylacetamide (DMAC) 32.0%, acetic acid 44.6%, N-methylacetamide 29.0%, and acetamide 17.4%.

EXAMPLE 11

A mixture of acetonitrile (12.33 g, 0.3003 mol), methanol (48.06 g, 1.50 mol), and water (1.80 g, 0.0999 mol) was placed in a stainless steel autoclave of 300 mL internal volume. The reactor was sealed, and the reaction mixture was purged with nitrogen through a dip tube for 30 minutes. The reactor was then heated to 350° C., and the reaction mixture was stirred vigorously for 4.5 hours. The temperature of the reaction mixture reached 382° C. during this time. The reactor was then cooled, and the reaction mixture was analyzed by gas chromatography. Conversion of methanol was 31.5% and conversion of acetonitrile was 78.7%. Product selectivities (based on acetonitrile) were as follows: methyl acetate 37.1%, N,N-dimethylacetamide (DMAC) 2.8%, acetic acid 22.1% N-methylacetamide 13.3%, and acetamide 11.8%.

Note that much acetic acid is made at a methanol-to-acetonitrile ratio of 2. Unless this is a particularly desired by-product, lower ratios are preferred because this acid is difficult to separate. At a ratio of 5 even more acetic acid is made and a large amount becomes esterified to methyl acetate. Moreover, DMAC selectivity is deleteriously affected.

Examples 12-15 were effected under the same conditions of Example 9 except that the amount of water was varied. These examples 9 and 12-15 show the effect of varying the amount of water in relation to the RCN charged.

EXAMPLE 12

A mixture of acetonitrile (31.60 g, 0.7697 mol), methanol (32.05 g, 1.0002 mol), and water (1.40 g, 0.0777 mol) was placed in a stainless steel autoclave of 300 mL internal volume. The reactor was sealed, and the reaction mixture was purged with nitrogen through a dip tube for 30 minutes. The reactor was then heated to 350° C., and the reaction mixture was stirred vigorously for 4.5 hours. The temperature of the reaction mixture reached 385° C. during this time. The reactor was then cooled, and the reaction mixture was analyzed by gas chromatography. Conversion of methanol was 71.0% and conversion of acetonitrile was 60.9%. Product selectivities (based on acetonitrile) were as follows; methyl acetate 16.8%, N,N-dimethylacetamide (DMAC) 4.1%, acetic acid 10.8%, N-methylacetamide 19.5%, and acetamide 31.1%.

EXAMPLE 13

A mixture of acetonitrile (31.59 g, 0.7695 mol), methanol (32.05 g, 1.0002 mol), and water (2.80 g, 0.1554 mol) was placed in a stainless steel autoclave of 300 mL internal volume. The reactor was sealed, and the reaction mixture was purged with nitrogen through a dip tube for 30 minutes. The reactor was then heated to 350° C., and the reaction mixture was stirred vigorously for 4.5 hours. The temperature of the reaction mixture reached 385° C. during this time. The reactor was then cooled, and the reaction mixture was analyzed by gas chromatography. Conversion of methanol was 86.9% and conversion of acetonitrile was 75.7%. Product selectivities (based on acetonitrile) were as follows: methyl acetate 3.5%, N,N-dimethylacetamide (DMAC) 25.3%, acetic acid 19.4%, N-methylacetamide 28.9%, and acetamide 30.9%.

EXAMPLE 14

A mixture of acetonitrile (31.58 g, 0.7693 mol), methanol (32.05 g, 1.0002 mol), and water (6.96 g, 0.3863 mol) was placed in a stainless steel autoclave of 300 mL internal volume. The reactor was sealed, and the reaction mixture was purged with nitrogen through a dip tube for 30 minutes. The reactor was then heated to 350° C., and the reaction mixture was stirred vigorously for 4.5 hours. The temperature of the reaction mixture reached 386° C. during this time. The reactor was then cooled, and the reaction mixture was analyzed by gas chromatography. Conversion of methanol was 90.2% and conversion of acetonitrile was 89.3%. Product selectivities (based on acetonitrile) were as follows: methyl acetate 0.6%, N,N-dimethylacetamide (DMAC) 25.8%, acetic acid 9.5%, N-methylacetamide 30.9%, and acetamide 24.2%.

EXAMPLE 15

A mixture of acetonitrile (31.61 g, 0.7700 mol), methanol (32.04 g, 0.9999 mol), and water (13.87 g, 0.7699 mol) was placed in a stainless steel autoclave of 300 mL internal volume. The reactor was sealed, and the reaction mixture was purged with nitrogen through a dip tube for 30 minutes. The reactor was then heated to 350° C., and the reaction mixture was stirred vigorously for 4.7 hours. The temperature of the reaction mixture reached 384° C. during this time. The reactor was then cooled, and the reaction mixture was analyzed by gas chromatography. Conversion of methanol was 94.9% and conversion of acetonitrile was 94.6%. Product selectivities (based on acetonitrile) were as follows: methyl acetate 0.7%, N,N-dimethylacetamide (DMAC) 22.4%, acetic acid 14.7%, N-methylacetamide 36.2%, and acetamide 17.8%.

EXAMPLE 16

A mixture of acetonitrile (31.58 g, 0.7693 mol), methanol (32.03 g, 0.9996 mol), and water (4.61 g, 0.2559 mol) was placed in a stainless steel autoclave of 300 mL internal volume. The reactor was sealed, and the reaction mixture was purged with nitrogen through a dip tube for 30 minutes. The reactor was then heated to 350° C., and the reaction mixture was stirred vigorously for 3.5 hours. The temperature of the reaction mixture reached 402° C. during this time. The reactor was then cooled, and the reaction mixture was analyzed by gas chromatography. Conversion of methanol was 90.2% and conversion of acetonitrile 84.6%. Product selectivities (based on acetonitrile) were as follows: methyl acetate 1.0%, N,N-dimethylacetamide (DMAC) 30.5%, acetic acid 13.5%, N-methylacetamide 26.9%, and acetamide 22.9%.

EXAMPLE 17

A mixture of acetonitrile (0.6156 mol), ethanol (0.8001 mol), and water (0.2065 mol) was placed in a stainless steel autoclave of 300 mL internal volume. The reactor was sealed, and the reaction mixture was purged with nitrogen through a dip tube for 30 minutes. The reactor was then heated and the reaction mixture was stirred vigorously. The temperature of the reaction mixture reached 364° C., and the reaction mixture was stirred for 4 hours at that temperature. The reactor was then cooled, and the reaction mixture was analyzed by gas chromatography. Conversion of ethanol was 36.8% and conversion of acetonitrile was 44.3%. Product yields (based on acetonitrile) were as follows: ethyl acetate 19.9%, N,N-diethylacetamide 0.2%, acetic acid 0.9%, N-ethylacetamide 2.6%, and acetamide 12.2%.

COMPARATIVE EXAMPLE F

A mixture of acetonitrile (0.6195 mol) and ethanol (0.8001 mol) was placed in a stainless steel autoclave of 300 mL internal volume. The reactor was sealed, and the reaction mixture was purged with nitrogen through a dip tube for 30 minutes. The reactor was then heated and the reaction mixture was stirred vigorously. The temperature of the reaction mixture reached 364° C., and the reaction mixture was stirred for 4 hours at that temperature. The reactor was then cooled, and the reaction mixture was analyzed by gas chromatography. Conversion of ethanol was 36.2% and conversion of acetonitrile was 19.7%. Product yields (based on acetonitrile) were as follows: ethyl acetate 8.4%, N,N-diethylacetamide 0.1%, acetic acid 1.1%, N-ethylacetamide 0.6%, and acetamide 2.6%.

EXAMPLE 18

A mixture of acetonitrile (0.0289 mol), methanol (0.0375 mol), $ZnCl_2$ (0.578 mmol), and water (0.0289 mol) was placed in a tubular stainless steel pressure vessel of 12 mL internal volume. The reaction mixture was purged with nitrogen for 30 minutes, and the reactor was sealed. The reactor was then heated to 310° C. for 20 minutes. The reactor was then cooled, and the reaction mixture was analyzed by gas chromatography. Conversion of methanol was 52.1% and conversion of acetonitrile was 67.4%. Product yields (based on acetonitrile) were as follows: methyl acetate 20.8%, acetic acid 3.8%, N,N-dimethylacetamide 1.8%, N-methylacetamide 12.4%, acetamide 16.1%.

COMPARATIVE EXAMPLE G

A mixture of acetonitrile (0.0346 mol), methanol (0.0465 mol), and $ZnCl_2$ (0.692 mmol) was placed in a tubular stainless steel pressure vessel of 12 mL internal volume. The reaction mixture was purged with nitrogen for 30 minutes, and the reactor was sealed. The reactor was then heated to 310° C. for 20 minutes. The reactor was then cooled, and the reaction mixture was analyzed by gas chromatography. Conversion of methanol was 46.6% and conversion of acetonitrile was 26.1%. Product yields (based on acetonitrile) were as follows: methyl acetate 11.8%, acetic acid 0%, N,N-dimethylacetamide 0.3%, N-methylacetamide 2.9%, acetamide 2.6%.

EXAMPLE 19

A mixture of acetonitrile (0.0134 mol), isopropyl alcohol (0.0271 mol), and water (0.0405 mol) was placed in a tubular stainless steel pressure vessel of 12 mL internal volume. The reaction mixture was purged with nitrogen for 30 minutes, and the reactor was sealed. The reactor was then heated to 360° C. for 4 hours. The reactor was then cooled, and the reaction mixture was analyzed by gas chromatography. Conversion of isopropyl alcohol was 96.0% and conversion of acetonitrile was 93.2%. Yield (based on acetonitrile) of N-isopropylacetamide was 2.1%.

COMPARATIVE EXAMPLE H

A mixture of acetonitrile (0.0246 mol) and isopropyl alcohol (0.0496 mol) was placed in a tubular stainless steel pressure vessel of 12 mL internal volume. The reaction mixture was purged with nitrogen for 30 minutes, and the reactor was sealed. The reactor was then heated to 360° C. for 6 hours. The reactor was then cooled, and the reaction mixture was analyzed by gas chromatography. Conversion of isopropyl alcohol was 67.7% and conversion of acetonitrile was 35.0%. Yield (based on acetonitrile) of N-isopropylacetamide was 0.4%.

EXAMPLE 20

A mixture of acetonitrile (0.0149 mol), t-butyl alcohol (0.0298 mol), and water (0.0044 mol) was placed in a tubular stainless steel pressure vessel of 12 mL internal volume. The reaction mixture was purged with nitrogen for 30 minutes, and the reactor was sealed. The reactor was then heated to 360° C. for 6 hours. The reactor was then cooled, and the reaction mixture was analyzed by gas chromatography. Conversion of t-butyl alcohol was 88.3% and conversion of acetonitrile was 40.6%. Yield (based on acetonitrile) of N-t-butylacetamide was 23.3%.

COMPARATIVE EXAMPLE I

A mixture of acetonitrile (0.0151 mol) and t-butyl alcohol (0.0309 mol) was placed in a tubular stainless steel pressure vessel of 12 mL internal volume. The reaction mixture was purged with nitrogen for 30 minutes, and the reactor was sealed. The reactor was then heated to 359° C. for 6 hours. The reactor was then cooled, and the reaction mixture was analyzed by gas chromatography. Conversion of t-butyl alcohol was 97.5% and conversion of acetonitrile was 53.3%. No N-t-butylacetamide was found in the product mixture.

EXAMPLE 21

A mixture of acetonitrile (0.0149 mol), n-butyl alcohol (0.0298 mol), and water (0.0050 mol) was placed in a tubular stainless steel pressure vessel of 12 mL internal volume. The reaction mixture was purged with nitrogen for 30 minutes, and the reactor was sealed. The reactor was then heated to 360° C. for 6.4 hours. The reactor was then cooled, and the reaction mixture was analyzed by gas chromatography. Conversion of n-butyl alcohol was 62.8% and conversion of acetonitrile was 92.4%. Product yields (based on acetonitrile) were as follows: n-butyl acetate 4.7%, acetic acid 1.2%, N,N-di-n-butylacetamide 0.15%, N-n-butylacetamide 1.0%, acetamide 0.9%.

COMPARATIVE EXAMPLE J

A mixture of acetonitrile (0.0153 mol) and n-butyl alcohol (0.0306 mol) was placed in a tubular stainless steel pressure vessel of 12 mL internal volume. The reaction mixture was purged with nitrogen for 30 minutes, and the reactor was sealed. The reactor was then heated to 360° C. for 5.9 hours. The reactor was then cooled, and the reaction mixture was analyzed by gas chromatography. Conversion of n-butyl alcohol was 81.2% and conversion of acetonitrile was 77.6%. Product yields (based on acetonitrile) were as follows: n-butyl acetate 6.3%, acetic acid 0.5%, N,N-di-n-butylacetamide 0.15%, N-n-butylacetamide 0.8%, acetamide 2.2%.

EXAMPLE 22

A mixture of isobutyronitrile (0.0203 mol), methanol (0.0418 mol), and water (0.0089 mol) was placed in a tubular stainless steel pressure vessel of 12 mL internal volume. The reaction mixture was purged with nitrogen for 30 minutes, and the reactor was sealed. The reactor was then heated to 360° C. for 7.1 hours. The reactor was then cooled, and the reaction mixture was analyzed by gas chromatography. Conversion of methanol was 47.4% and conversion of isobutyronitrile was 62.2%. Product yields (based on isobutyronitrile) were as follows: N,N-dimethylisobutyramide 0.42%, N-methylisobutyramide 7.9%, isobutyramide 11.4%.

COMPARATIVE EXAMPLE K

A mixture of isobutyronitrile (0.0220 mol) and methanol (0.0437 mol) was placed in a tubular stainless steel pressure vessel of 12 mL internal volume. The reaction mixture was purged with nitrogen for 30 minutes, and the reactor was sealed. The reactor was then heated to 358° C. for 7.25 hours. The reactor was then cooled, and the reaction mixture was analyzed by gas chromatography. Conversion of methanol was 51.9% and conversion on isobutyronitrile was 54.5%. Product yields (based on isobutyronitrile) were as follows:

N,N-dimethylisobutyramide 0.065%, N-methylisobutyramide 1.5%, isobutyramide 2.2%.

EXAMPLE 23

A mixture of trimethylacetonitrile (0.0190 mol), methanol (0.0381 mol), and water (0.0061 mol) was placed in a tubular stainless steel pressure vessel of 12 mL internal volume. The reaction mixture was purged with nitrogen for 30 minutes, and the reactor was sealed. The reactor was then heated to 369° C. for 7 hours. The reactor was then cooled, and the reaction mixture was analyzed by gas chromatography. Conversion of methanol was 99.9% and conversion of trimethylacetonitrile was 54.8%. Product yields (based on trimethylacetonitrile) were as follows: N-methylpivalamide 0.84%, pivalamide 1.4%, methyl trimethylacetate 14.8%.

COMPARATIVE EXAMPLE L

A mixture of trimethylacetonitrile (0.0197 mol) and methanol (0.0396 mol) was placed in a tubular stainless steel pressure vessel of 12 mL internal volume. The reaction mixture was purged with nitrogen for 30 minutes, and the reactor was sealed. The reactor was then heated to 362° C. for 7.7 hours. The reactor was then cooled, and the reaction mixture was analyzed by gas chromatography. Conversion of methanol was 99.9% and conversion of trimethylacetonitrile was 47.5%. Product yields (based on trimethylacetonitrile) were as follows: N-methylpivalamide 0.14%, pivalamide 1.5%, methyl trimethylacetate 0.45%.

EXAMPLE 24

A mixture of benzonitrile (0.0173 mol), methanol (0.0340 mol), and water (0.0050 mol) was placed in a tubular stainless steel pressure vessel of 12 mL internal volume. The reaction mixture was purged with nitrogen for 30 minutes, and the reactor was sealed. The reactor was then heated to 364° C. for 6.6 hours. The reactor was then cooled, and the reaction mixture was analyzed by gas chromatography. The product mixture contained N,N-dimethylbenzamide, N-methylbenzamide, and benzamide.

As will be evident to those skilled in the art various modifications of this invention can be made or followed in the light of the foregoing disclosure and discussion without departing from the spirit and scope of the disclosure or from the scope of the claims.

I claim:

1. A method which comprises the reaction in a reaction zone of a nitrile, RCN, with a hydroxyl compound, R'OH, in the presence of water introduced into the reaction zone from outside the reaction zone as a promoter in the amount of more than 0.15 mole and up to 10 moles, per mole of RCN introduced to the reaction zone, thereby producing a reaction mixture containing at least one amide selected from R-CONHR' and R—CON(R')$_2$, wherein each of R and R' is an independently selected hydrocarbyl group containing 1 to 30 carbon atoms and no acetylenic unsaturation and no catalyst for said reaction other than said water promoter is introduced into said reaction zone.

2. A method according to claim 1 which comprises the reaction in a reaction zone of acetonitrile with methanol in the presence of water introduced into the reaction zone in the amount of more than 0.15 mole and up to 10 moles, per mole of acetonitrile introduced into the reaction zone, thereby producing a reaction mixture containing N,N-dimethylacetamide.

3. A method of claim 1 wherein the mole ratio of R'OH to RCN introduced into the reaction zone is in the range of 0.1 to 20.

4. A method of claim 10 wherein said mole ratio is in the range 1 to 10.

5. A method of claim 1 wherein each of R and R' contains 1 to 12 carbon atoms.

6. A method of claim 2 wherein the mole ratio of methanol to acetonitrile introduced into the reaction zone is in the range of 0.1 to 20.

7. A method of claim 6 wherein said mole ratio is in the range 1 to 10.

8. A method according to claim 1 which comprises the reaction in a reaction zone of acetonitrile with ethanol in the presence of water introduced into the reaction zone in the amount of more than 0.15 mole and up to 10 moles, per mole of acetonitrile introduced into the reaction zone, thereby producing a reaction mixture containing N,N-diethylacetamide.

9. A method according to claim 1 which comprises the reaction in a reaction zone of acetonitrile with isopropanol in the presence of water introduced into the reaction zone in the amount of more than 0.15 mole and up to 10 moles, per mole of acetonitrile introduced into the reaction zone, thereby producing a reaction mixture containing N-isopropylacetamide.

10. A method according to claim 1 which comprises the reaction in a reaction zone of acetonitrile with t-butyl alcohol in the presence of water introduced into the reaction zone in the amount of more than 0.15 mole and up to 10 moles, per mole of acetonitrile introduced into the reaction zone, thereby producing a reaction mixture containing N-t-butylacetamide.

11. A method according to claim 1 which comprises the reaction in a reaction zone of isobutyronitrile with methanol in the presence of water introduced into the reaction zone in the amount of more than 0.15 mole and up to 10 moles, per mole of acetonitrile introduced into the reaction zone, thereby producing a reaction mixture containing N-methylisobutyramide.

12. A method according to claim 1 which comprises the reaction in a reaction zone of acetonitrile with n-butyl alcohol in the presence of water introduced into the reaction zone in the amount of more than 0.15 mole and up to 10 moles, per mole of acetonitrile introduced into the reaction zone, thereby producing a reaction mixture containing N-n-butylacetamide.

13. A method according to claim 1 which comprises the reaction in a reaction zone of trimethylacetonitrile with methanol in the presence of water introduced into the reaction zone in the amount of more than 0.15 mole and up to 10 moles, per mole of acetonitrile introduced into the reaction zone, thereby producing a reaction mixture containing N-methylpivalamide.

14. A method according to claim 1 which comprises the reaction in a reaction zone of benzonitrile with methanol in the presence of water introduced into the reaction zone in the amount of more than 0.15 mole and up to 10 moles, per mole of acetonitrile introduced into the reaction zone, thereby producing a reaction mixture containing N,N-dimethylbenzamide and N-methylbenzamide.

* * * * *